United States Patent [19]

Prince et al.

[11] Patent Number: 5,244,794
[45] Date of Patent: Sep. 14, 1993

[54] FLAVOR COMPOUNDS FROM ALLIUM ROOT CULTURES

[75] Inventors: Christopher Prince; Michael L. Shuler, both of Ithaca, N.Y.

[73] Assignee: Cornell Research Foundation, Inc., Ithaca, N.Y.

[21] Appl. No.: 724,572

[22] Filed: Jun. 28, 1991

Related U.S. Application Data

[63] Continuation-in-part of Ser. No. 325,413, Mar. 17, 1989, abandoned.

[51] Int. Cl.$^5$ .......................... C12P 13/12; C12P 1/00
[52] U.S. Cl. ........................................ 435/113; 435/41
[58] Field of Search .......................... 435/41, 261, 113

[56] References Cited

U.S. PATENT DOCUMENTS 4,371,551 2/1983 Fulger et al. ........................ 426/28
4,613,507 9/1986 Fulger et al. ........................ 426/68

OTHER PUBLICATIONS

Evans, et al., Ed. *Handbook of Plant Cell Culture*, vol. 1, Techniques for Propagation and Breeding, MacMillan Publishing Co., 1983, pp. 205-206, pp. 63-65.
Krikorian, A. D. et al., Phytomorphology, 209-211 (1968).
Klein, Richard M. et al., Phytomorphology, 18:204-206 (1968).
White, P. R. Plant Physiol., 9:585-600 (1934).
Ramagopal, S., J. Plant Physiol., 132:245-249 (1988).
Freeman, G. G., et al., Plant Science Letters, 3:121-125 (1974).
Davey, M. R., et al., Plant Science Letters, 3:113-120 (1974).
Dolezel, J. et al., Biological Plantarum (Praha), 26(4):293-298 (1984).
Malpathal, N. P., et al., Plant Cell Reports, 5:446-447 (1986).
Selby, C. et al., New Phytol., 83:351-361 (1979).
Selby, C. et al., Ann. Bot., 40:911-918 (1976).
Selby, C. et al., New Phytol., 84:307-312 (1980).
Granroth, Bengt, Annales Academiae Scientarium Fennicae, Aelsinki 1970, pp. 1-69.
Turnbull, A. et al., New Phytol, 85:483-487 (1980).
Turnbull, A. et al., New Phytol, 87:257-268 (1981).
Sejtli, J., Starch/Starke 34 #11, 379-385 (1984).
Cho, T. et al., "Integrated Product Recovery and Bioconversion Reactors", presented in part at the 7yh Symposium on the Biotechnology for Fuels and Chemicals, Gatlinburg, TN in 1985.
Payne and Shuler, Biotechnology & Engineering Symp. No. 15 (9185) pp. 633-639.
Payne et al., Biotechnology Letters, 10(3):187-192 (1988).
Payne and Shuler, Biotechnology and Bioengineering, 31:922-928 (1988).
Payne et al., Biotechnology and Engineering, 31:905-912 (1988).
Prince, C. L., et al., Abstract, Division of Microbial and Biochemical Technology, Division Newsletter, Abstract No. 26 (1988) Third Chemical Congress of North America, Toronto, Canada Jun. 5-10, 1988.

(List continued on next page.)

*Primary Examiner*—Douglas W. Robinson
*Assistant Examiner*—Kristin K. Larson

[57] ABSTRACT

Root organ cultures of the monocot genus Allium were successfully grown in culture medium. In a preferred bioreactor system, the roots themselves can be grown and harvested as a source of various Allium flavors and/or the growing roots can be reacted with various nutrients to produce Allium flavor compounds independent of the root harvesting. The root cultures of the present invention produce quantities of onion and onion-like flavor compounds comparable to those found in onion bulbs.

Flavor precursors are converted to isolable flavors via enzyme catalysis such as C-S lyase enzyme. Production of Allium flavor precursors is improved by addition of chemical additives to the root organ culture. The product profile of the Allium flavor materials produced can be controlled by adjusting the levels of and type of chemical additives.

4 Claims, 5 Drawing Sheets

OTHER PUBLICATIONS

"Onion's roots made to Yield better flavors than its oils", Cornell Chronicle Jun. 9, 1988.

Lancaster, Jane E. et al., Phytochemistry, vol. 27, No. 7 pp. 2123–2124 1988, "Production of Flavor Precurssors (s-alkenyl–L–cysteine sulfoxides) in Photomixotrophic Callus of Garlic".

DiCosmo et al., Trends in Biotechnology, 3(No. 5):110–111 (1985).

Collin et al., in *Secondary Metabolism in Plant Cell Cultures*, Morris et al., eds., pp. 54–55 (1986), Cambridge U. Press.

Collin, H. A. and Musker, D. "Allium Compounds", pp. 475–493 in Cell Culture and Somatic Cell Genetics, vol. 5, Phytochemicals in Plant Cell Cultures, Academic Press Copyright 1988.

Shuler, Michael L., Proc. APBIOCHEC 90 Apr. 22–25, 1990 Kyungju, Korea "Some Bioractor Considerations for Plant Tissue Culture".

Prince, C. L., Yamada, U. and Shuler, M. L., Unpublished Prepared for presentation AICHE 1990 Annual Meeting, Chicago, IL, Nov. 11–16, 1990 "Flavor Compound Production from Allium Sp. Root Organ Cultures".

Abstract (Extended Abstract for inclusion in the meeting Abstract Book) American Institute of Chemical Engineers, Nov. 11, 1990 "Flavor Compound Production from Allium Sp. Root Organ Cultures".

FLAVOR COMPOUNDS FROM ALLIUM ROOT CULTURES

This invention was made in part under NSF Grant No. 85-03183. The U.S. Government has certain rights to this invention.

This application is a continuation-in-part application of copending application Ser. No. 07/325,413, filed Mar. 17, 1989, now abandoned.

The present invention relates to root organ tissue culture and to the production of secondary metabolites from root organ cultures. More specifically, the invention relates to the cultivation of the roots of various species in the genus Allium (onion, garlic, etc.) and their use in bioreactors for the sustained production of Allium type flavors and flavor precursors.

BACKGROUND OF THE INVENTION

The use of undifferentiated cell cultures suffers from various constraints including:

1. Many undifferentiated cell culture systems do not display significant secondary biosynthesis and require a level of structural differentiation more closely akin to that found in the intact plant.

2. Often undifferentiated cell culture systems display considerable genetic instability during prolonged culturing. Diminished production of secondary metabolites is commonly observed.

3. Fine suspensions are often difficult to achieve, particularly ones retaining high organogenic potential. Large aggregates usually have slow growth rates; for example, *A. cepa* root cultures grow faster than submerged callus-like aggregates.

Freeman et al (1974) and Selby and Collin (1976) have demonstrated that callus cultures of *Allium cepa* accumulate only very small amounts of the desired flavor precursor compounds. The same has also been shown for *Allium sativum* (Malpathak and David, 1986). Redifferentiated root-like structures, however, were biosynthetically capable (Freeman, 1974). Efforts aimed at enhancing flavor precursor levels by clonal selection have failed (Selby and Collin, 1976). Likewise, previous attempts to increase the productivity of undifferentiated onion cultures by the addition of biosynthetic precursors such as cysteine, valine, sulfate, serine and methacrylic acid, have failed (Selby et al., 1980). Granroth (1970) and Turnbull et al (1981) have observed rapid uptake and transformation of labelled biosynethetic precursors by excised onion shoot tips. Krikorian and Katz (1967), demonstrated that it is possible to grow onion roots in culture in a fully differentiated state, however, no attempt was made to achieve or characterize their secondary biosynthetic potential. Klein and Edsall reported the isolation of callus cultures from seeds of *Allium cepa*.

Because of the limitations on the use of undifferentiated cell cultures for secondary metabolite production there is a need for an improved method for producing such secondary metabolites from organ culture and particularly root cultures. Further, there is a need to produce viable root cultures capable of yielding a uniform and genetically stable differentiated roots in high yield The present bioprocess and reactor utilizes root cultures for the growth of roots and production of flavorants and flavor precursors.

BRIEF SUMMARY OF THE INVENTION

The present invention relates to stable, differentiated root cultures of the genus Allium (onion and related species) and their continuous growth in vitro.

One aspect is a root organ culture capable of producing substantial amounts of Allium flavors or flavor precursors wherein said culture is obtained, in one preferred mode, by culturing a root tip derived from an aseptic and virus-free Allium shoot apical meristem, consisting essentially of organized meristem tissue, in the presence of a hormone adapted to produce a genetically stable differentiated root.

Another aspect of the invention relates to the productivity enhancement of root cultures using various promoter additives including hormones, enzymes, elicitors and chemical enhancers to increase the production of Allium flavor precursors.

A further aspect of the invention relates to a bioreactor and process for the continuous production of such root cultures and for the production of Allium flavor precursors and their conversion to Allium flavors.

DETAILED DESCRIPTION OF THE INVENTION

Figure 1:
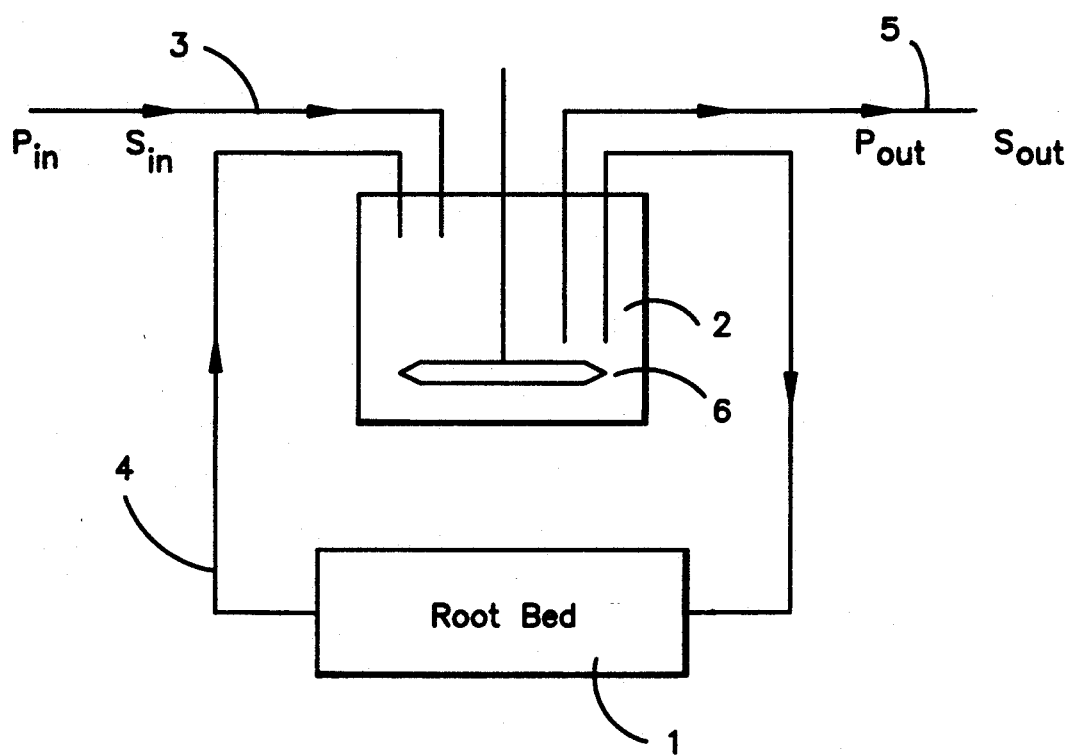
FIG. 1 is a schematic representation of a simple root reactor wherein the active cultured root is immobilized with respect to the recycle vessel containing nutrient and product streams.

Root cultures of the monocot genus Allium were successfully grown in culture medium It has now been found that various onion and garlic flavors can be advantageously produced using cultures of plant roots rather than by use of undifferentiated cell cultures (suspension or callus). In contrast to undifferentiated cell cultures, the plant organs such as roots can be adapted to produce substances called secondary metabolite compounds that are useful flavorings or drugs. Plant organ cultures are often genetically more stable during growth and are easier to immobilize in bioreactors than are cell suspensions. Immobilized bioreactors are culture growth chambers in which living cells or tissues are fed nutrients and release secondary compounds such as flavor compounds or drugs into the liquid medium passing through the culture.

For purposes of the present invention, the terms cultured root, root culture and tissue-cultured root are used interchangeably to mean an organized, viable, preferably non-polyploidy, plant root organ sterily (aseptically) grown in a nutrient medium sufficient to foster root growth without growth of other plant parts i.e. stems, leaves, flowers, callus, shoots etc. Such stable cultured roots maintain their genetic integrity. This is contrasted with other growth modes which undergo severe genetic alterations.. The differentiated cultured roots of the invention are distinct and different from callus tissue, stems, leaves, shoots and roots derived from callus and/or other undifferentiated tissue. A preferred source of such growth stable and substantially genetically pure differentiated root organs is a sterile (aseptic) and virus-free meristem Allium shoot apical meristem as described herein.

An advantageous process for producing a viable, differentiated, non-polyploidy tissue-cultured root of the monocot genus Allium comprises the steps of:

Culturing a root tip derived from a sterile and virus-free Allium shoot apical meristem; wherein said meristem, consisting essentially of organized meristem tissue, is cultured either in a hormone-free nutrient or in a nutrient containing small amounts of hormone; and said root tip is cultured in a nutrient containing a hormone sufficient to promote differentiated root growth to produce a viable and genetically-stable cultured root.

More specifically, the above process includes the steps of:

a. culturing sterile and virus-free Allium shoot apical meristem, either in a hormone-free nutrient or a nutrient containing small amounts of hormone to produce an Allium derived plantlet; said meristem tissue consisting essentially of organized meristem tissue;

b. excising a root tip from said plantlet;

c. culturing the root tip in a nutrient containing a hormone sufficient to promote differentiated root growth to obtain a viable and genetically-stable cultured root.

This process is particularly advantageous when seeds are unknown or unavailable.

An alternative process may be used when Allium seeds are readily available, namely the process which comprises a. germinating a sterilized Allium seed and culturing the germinated seed in a hormone-free nutrient medium to produce an Allium plant comprising a root;

b. excising a root tip from the root;

c. culturing the excised root tip in a nutrient medium in the presence of a small amount of hormone adapted to foster the growth of the said root;

d. sequentially transferring the growing root to fresh medium having increasingly greater amounts of the said hormone until a stable cultured root is obtained.

As used herein, "root growth to the substantial exclusion of callus growth" means that only differentiated root growth occurs, preferably without root anomalies. Additives and conditions are chosen to avoid genetic variation, i.e. polyploidy, resulting from undifferentiated callus growth.

In the present system, Allium roots have been cultured and grown to produce flavor precursors which subsequently yield flavors characteristic of the individual Allium species (i.e. onion, garlic, leek, etc.).

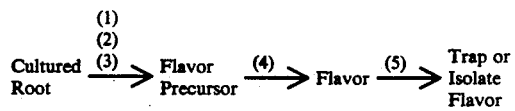

(1) Nutrients; (2) Elicitor (3) Chemical Enhancer (4) Enzyme (5) Flavor Entrapping Means Allium species that are useful in the practice of this invention include: *A. cepa* (onion); *A. niponicum* ("nobiru"); *A. sativum* (garlic); *A. wakegi* ("wakegi"); *A. vineale* (wild garlic); *A. porrum* (leek); *A. fistulosum* ("negi" Welch onion); *A. bakeri; A. ascolonicum* (shallot); *A. tuberosum* ("chinese chives"); *A. tricoccum* ("wild leek"); *A. schoenoprasum* (chive) and the like.

Precursor compounds of interest are simple cysteine sulfoxide derivatives:

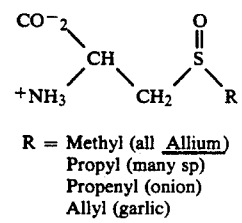

R = Methyl (all Allium)
Propyl (many sp)
Propenyl (onion)
Allyl (garlic)

These compounds are very hydrophilic. They are also unstable in alkali and are somewhat difficult to recrystallize. They have no significant odor or flavor and are converted to active compounds only upon damaging the tissue (see below). In contrast to most other plant secondary metabolites which are stored in the large central vacuole, these compounds are believed to be stored in cytoplasm.

Biosynthetic Pathway

Biosynthesis is described by the following overall scheme:

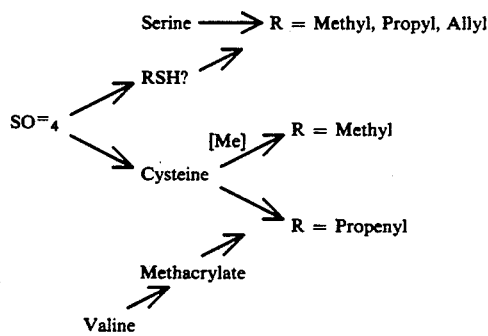

Flavor Generation

When tissue is damaged, allinase enzyme, compartmentalized into the vacuole, acts on precursor substrate to form the flavor, lachrymatory, antibacterial and antifungal compounds, etc.

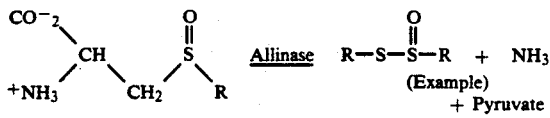

The first stable compounds formed from the methyl, propyl and allyl derivatives are the corresponding thiosulfinates shown above. For onion, the propenyl derivative reacts to form thiopropanal S-oxide, the lachrymatory factor. All of these initially formed compounds in combination with small amounts of secondary reaction products, characterize the sensory notes of fresh onion or garlic.

Secondary Reactions

Thiosulfinates are unstable and can dehydrate or disproportionate to disulfides and thiosulfonates:

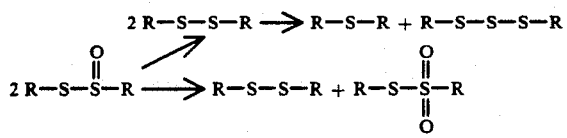

Disulfides undergo thiol interchange reactions to give rise to monosulfides, trisulfides etc., and mixed (R1-S-S-R2) disulfides. In onion, the degradation products of thiopropanal S-oxide result in complex product profiles. Reactive aldehydes are formed which are capable of aldol condensations with themselves and with decarboxylated pyruvate from the original allinase reaction. The positive reduction potential of the cytoplasm further permits reduction of aldehydes to hydroxy groups in any of the intermediates. These diverse reactions proceed within minutes to hours and as a result, onion and garlic oils consist only of such polysulfide and other degradation products and therefore do not resemble fresh product chemically. Any system capable of exerting control over these secondary reactions could give rise to products more closely approximating "fresh" quality. Interestingly, the quality of pharmaceutical garlic products is directly related to the quality of retained allyl thiosulfinate.

Products

The relative polar or non-polar character of chemical species present is important from the point of view of separations. In contrast to the precursor compounds, the thiosulfinates (one oxygen) and disulfides (no oxygen), are somewhat hydrophobic. Hydrophilicity increases in order from disulfides to thiosulfonates.

The instant invention may be adapted to produce and harvest differentiated cultured roots having uniform quality and genetic purity and/or to produce Allium flavor precursors capable of being converted to Allium flavors.

Referring to the harvesting of the root cultures grown in a culture vessel bioreactor, the roots can be continuously or semicontinuously removed from the bioreactor. Thereafter roots can be incorporated directly in food products to provide the desired flavor. Roots can be used fresh, dried, or otherwise crushed, extracted and/or bound to suitable carriers.

In addition to root growth and harvesting, another aspect of the present invention relates to a process for the production of Allium flavor precursors and Allium flavors from cultured roots of the monocot genus Allium which comprises:

a) adding to a bioreactor a cultured Allium root adapted to the continuous or semicontinuous selective growth of root;

b) contacting the cultured root with a nutrient sufficient to foster selective root growth and to cause the root to produce an Allium flavor precursor;

c) optionally contacting the Allium flavor precursor with an enzyme such as C-S lyase to convert the Allium flavor precursor to an Allium flavor;

d) isolating the said flavor or Allium flavor precursor;

wherein the production of the Allium flavor precursor is enhanced by the addition to the reactor or the nutrient of one or more of promoter additives or enhancers selected from the group consisting of hormones, elicitors and chemical promoters; and wherein said cultured root is prepared as set forth above from a sterile Allium seed or from a sterile Allium shoot apical meristem.

For purposes of this invention, various promoter additives (enhancers) or combinations of additives may be used for accelerating and increasing the production of said secondary metabolite products. Such promoter additives are selected from the group consisting of hormone enhancers, elicitors and chemical enhancers (e.g. biosynthetic precursors) or mixtures thereof.

Examples of hormone enhancers used at 0.01 to 10 mg/liter of nutrient medium include auxins and cytokinins. Useful auxins include indole butyric acid (IBA); indole acetic acid (IAA); naphthalene acetic acid (NAA); 4-chloro IAA; 5,6-dichloro IAA; p-chlorophenoxyisobutyric acid; 2,4-dichlorophenoxyacetic acid (2,4-D); and phenyl acetic acid (PAA). Useful cytokinins include kinetin, 6-benzyladenine (BA); 6-(3-methyl-2-butenylamino) purine; zeatin; dihydrozeatin; and the like.

Elicitors useful in the process of this invention and for enhancing the production of secondary metabolite products include biotic elicitors and abiotic elicitors. Biotic elicitors include gluconopolymers, glycoproteins, low molecular weight organic acids and fungal material including fungal cell wall material. Abiotic elicitors include ultraviolet irradiation, salts of heavy metals, and chemical elicitors such as diethylaminoethyl dichlorophenyl ether and the like. Fungal elicitors including fungal carbohydrate elicitors and material derived from the cell wall of fungi such as *Phytophthora megasperma* and *Phytophthora cactorum* are particularly useful in the practice of this invention. A preferred fungal elicitor for onium flavors is *Phytophthora cactorum*.

Chemical promoter additives are useful for enhancing the production of metabolite products and may be used alone or with other promoter additives including the herein describe elicitors. Combinations of elicitors and chemical enhancers are particularly useful. Preferred combinations are those of fungal elicitors with chemical enhancers. Chemical promoters (enhancers) useful in the production of secondary metabolites are chemical compounds which are capable of being rapidly converted into the metabolite of interest and particularly those that are biosynthetic precursors of the target metabolite.

The "chemical enhancer additive" is distinct and different from and should not be confused with the term "flavor precursor" even though they often may be somewhat similar in structure In many cases, the chemical enhancer may itself be a "biosynthetic precursor" of the "flavor precursor".

The promoter additives including elicitors and chemical enhancers can be added directly to the reaction vessel or they can be added to the nutrient containing substrate. When the bioreactor comprises a multilayer bioreactor having an immobilized root culture layer, the fungal elicitor is preferably in close contact with the immobilized root culture and/or the elicitor may be immobilized.

The addition of chemical enhancer compound to the nutrient feed enhances (increased yield and rate) the production of secondary metabolites i.e. Allium species' flavor compounds. Examples of useful enhancer chemicals include: cysteine, glutathione, serine, methionine, valine, propylthiol, allylthiol and the like. For onion flavor products, cysteine is a preferred additive.

Another aspect of the invention relates to bioreactors for both growing Allium root cultures and for producing Allium flavors and flavor precursors derived by the reaction of said cultured roots with nutrients, elicitors and chemical enhancers and optionally containing an enzyme catalyst adapted to convert produced flavor precursors to Allium flavors.

Such a root bioreactor comprises:

a) a reaction vessel b) immobilized cultured roots of the Allium genus adapted for reaction with a nutrient to produce flavors and/or flavor precursors;

c) a substrate comprising a nutrient medium for reacting with said roots to produce one or more flavor precursors which can be converted to Allium flavors;

d) an immobilized enzyme capable of converting the flavor precursors to said flavors;

e) a means adapted to selectively trap, extract or adsorb the Allium flavors without trapping the flavor precursor; wherein the cultured roots are separated from the substrate as for example by means of a semipermeable membrane and from the said enzyme; and wherein said reactor further comprises one or more promoter additives to accelerate and increase the production of flavor precursors and flavor products in the reaction of nutrient with cultured roots, said promoter additives being selected from the group consisting of hormones, elicitors, and chemical enhancers or mixtures thereof.

For the bioreactor preparation of various Allium species flavors and flavor precursors it is contemplated to use chemical enhancer compounds having a structure similar or related to that of the Allium flavor or flavor precursor. Such compounds can be represented in part by the formula:

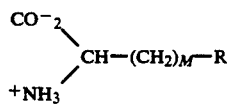

(I)

where M is 1 or 2; R is $R^1O-$, $R^1S-$, $R^1-CH(CH_3)-$ and the like and where the $R^1$ is H, $C_1-C_6$ lower alkyl or loweralkenyl radical. R can be varied to produce different flavor products depending on the specific root culture used. Propenyl radical is a preferred radical for onion species and allyl radical is a preferred radical for garlic species. Examples of useful chemical additives which enhance production of the various flavors and/or flavor precursors include cysteine, serine, methionine, valine and the like. For onion flavor products, cysteine is a preferred additive.

The bioreactor for the present invention can be simple or complex; it can be batch, semicontinuous or continuous as desired. FIG. 1 shows a continuous root culture bioreactor where P and S represent product and substrate concentrations respectively where the root bed (1) is isolated from the recycle vessel (2) containing inlet streams (3) for addition of nutrients, enzymes, elicitors and chemical enhancers biosynthetic (precursors), recirculation stream (4) for transport of reaction medium to and from the root bed (1), product exit and nutrient recycle streams (5) and having an agitation and aeration means (6).

Although the present invention can be performed in various reactor vessels, the preferred reactor is a bioreactor where one or more of the components are immobilized. For example, the growing cultivated roots can be immobilized by confining the roots within a multilayer semipermeable membrane reactor and preferably a multilayer reactor having multiple semipermeable membranes to define separate layers. Such layers include the cultured root layer, nutrient layers, and product layers. It is advantageous to use a simple macroporous screen (e.g. stainless steel) or a semipermeable membrane to separate the nutrient feed layer from the roots while allowing nutrients, elicitors and additives to pass into the root layer for reaction with the roots. A similar screen and/or a hydrophilic semipermeable membrane will suffice to separate the root layer from a product layer. Such membrane should be able to pass product from the root layer to the product layer from which the product can be isolated by various means.

Various known methods which can be used for product removal include extraction into organic solvent and resin adsorption. In the present case, precursor compounds are extremely water soluble, as are most of the other key medium components. Direct extraction is generally not preferred since it is relatively non-selective. Adsorption can be used on "amino columns" below pH 2. However, recovered flavor precursors have to be subsequently converted to flavor compounds. In a preferred system, flavor precursor production is combined with an enzymatic conversion to flavor compounds within a coupled immobilized cell/enzyme membrane reactor such as that shown in FIG. 2.

Figure 2:
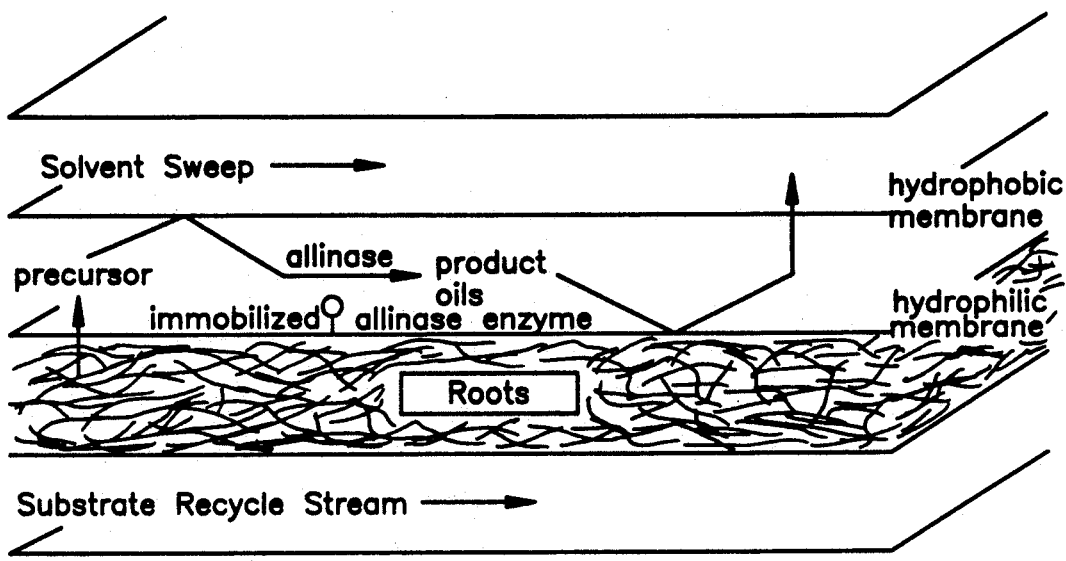
FIG. 2 is a schematic representation of root reactor coupled with an allinase (C-S lyase) enzyme membrane reactor.

When the root reactor and process requires an enzyme to convert a precursor product to a product, such as for example when the Allium root is contacted with a nutrient to yield an Allium type flavor precursor which can be transformed to an Allium flavor by reaction with an enzyme (i.e. C-S lyase), it is important to provide a separation means such as a hydrophobic semipermeable membrane which retains the enzyme and flavor precursor, but allows the product flavor to pass to a product stream. Alternatively the enzyme reactor can be configured in series (or in a separate loop) in a packed or fluidized bed arrangement followed in series by an adsorptive resin bed or solvent extractor. Such trapping of product may be accomplished by selective adsorption or entrapment means using solvents, selective molecular sieve, resin adsorbents and the like. One such system is shown in FIG. 2 having an immobilized root layer, a nutrient recycle layer, an immobilized allinase (C-S lyase enzyme) layer for converting the precursor flavor to a flavor product and a solvent sweep layer. The system depends on the type of semipermeable membranes used. The membrane (hydrophilic) separating the roots from the enzyme layer should allow passage of flavor precursor for reaction with the enzyme to flavor product. The membrane separating the solvent layer from the enzyme layer should prevent the solvent from entering the enzyme layer, should prevent the precursor from passing to the solvent layer but should selectively allow the passage of flavor product to pass to the solvent layer.

Figure 3:
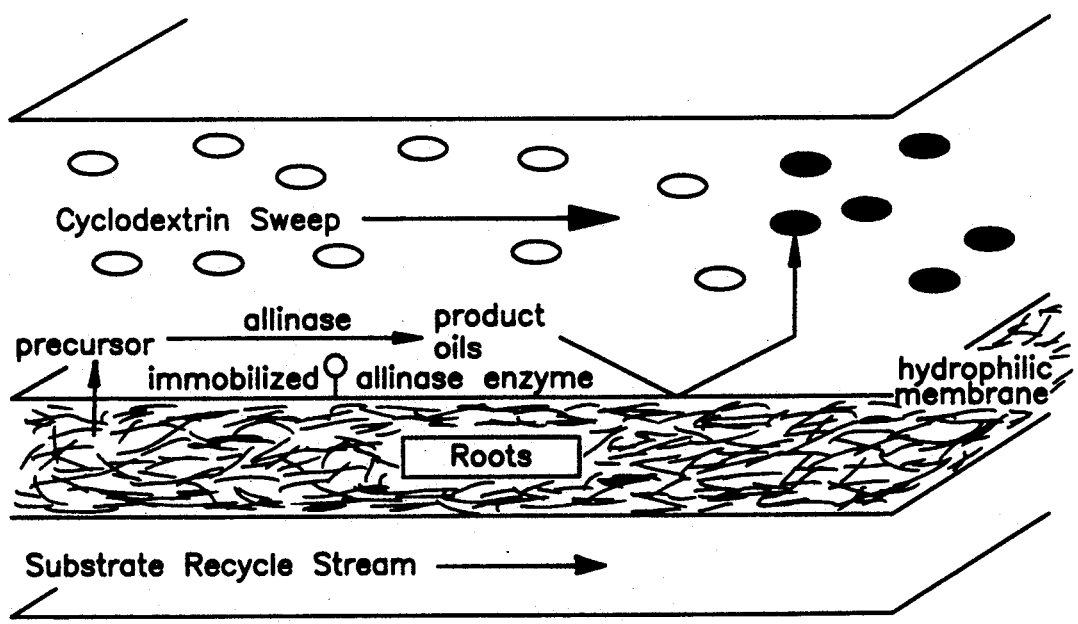
FIG. 3 is a schematic representation of a root reactor coupled with an allinase enzyme membrane reactor using a cyclodextrin sweep stream for scavenging or complexing the flavor product.

A variant of the reactor is shown in FIG. 3; the immobilized enzyme, the precursor flavor and the flavor product all reside in the same layer which additionally contains a means to selectively remove the flavor product. Product removal affects the reaction equilibrium and enhances product yield and rate. A preferred system utilizing the FIG. 3 configuration is one that involves complexation and stabilization of the first formed enzyme reaction products in the hydrophobic pocket of a cyclic molecule. A cyclodextrin containing aqueous sweep stream will suffice for this purpose and nicely avoids the organic solvent problem. Other examples of such entrapping means include ionic exchange resin, neutral resin and molecular sieves As shown in FIG. 2, use can be made of the differential solubility of products and reactants in the allinase catalyzed reaction In the allinase reaction compartment, hydrophilic reactants are "trapped" upon reaction to form hydrophobic products. For the scheme shown in FIG. 2, precursors should be very efficiently rejected at the hydrophobic membrane and thiosulfinate products may be somewhat rejected at the hydrophilic membrane, depending on the material chosen. In using an enzyme catalyst reaction for separation, selectivity should, in principle, be almost complete. When a solvent compartment is used, an extractant with a high partition coefficient for thiosulfinates (and lachrymator) is preferred.

Crude allinase enzyme can easily be prepared by $(NH_4)_2SO_4$ precipitation. In the allinase reactor compartment, soluble, gel entrapped, or covalently bound allinase can be employed. Various enzymes can be used for the conversion of flavor precursor to flavor product depending on the organ culture and the metabolite desired. These include C-S lyase enzymes from many sources including those from Allium species, as well as from fungal and bacterial species.

As indicated above, various semipermeable membranes can be used in defining the structure and layers of the multilayer membrane bioreactor. These include hydrophilic membranes, hydrophobic membranes and ion-exchange membranes. Suitable commercially available ion-exchange membranes include Nafion (DuPont) ion exchange resin, and the like. The flavor precursor and/or the Allium flavors can be isolated by a variety of separation methods known to the art. Such methods include semipermeable membranes, reverse osmosis membranes, entrapment or adsorption with ion exchange, neutral resins and cyclic structures having a hydrophobic pocket such as cyclodextrin and the like.

Plant Cell Culture Immobilization

Plant cell culture (organ culture) utilizes the plants own ability to create microenvironments favorable for directed biochemical differentiation and expression of secondary metabolic pathways. Unlike undifferentiated cell cultures, organ cultures retain desirable metabolic traits during non-selective culturing. The problem of genetic instability is reduced or eliminated when growth phase operations are carried out by direct shoot or root proliferation.

A further advantage of organ cultures over suspensions lies in their intrinsic compatibility with the engineering concept of immobilization. Plant cell cultures, in general, possess slow growth rates, making their specific costs as biocatalysts very high. In addition to the biological advantages that may be obtained, immobilization with continuous operation offers a number of process engineering advantages, particularly with respect to the "reuse" of expensive plant cell biomass. Differentiated organs represent a form of "self immobilized" cells which can show a natural form of high biosynthetic expression, arrested growth, and above all, product secretion. These are important considerations when cells are to be retained or "immobilized" within the reactor.

Preparation of Allium Organ Tissue

Large amounts of sterile biosynthetically active Allium organ tissue can best be obtained by growing root cultures directly rather than by redifferentiating undifferentiated cell aggregates, growing sterile seedlings or by sterilizing intact plant tissue. Overall growth rates are higher and biomass accumulation via root cultures give rise to less genetic instability and can be accomplished in the dark. Cultures are initiated from excised root tips either from sterile seedlings or from cultured shoot apical meristems which subsequently form roots. The latter technique is used with sexually sterile (no seed) varieties, and for wild species or others for which seeds could not easily be obtained.

In addition to the product and process benefits suggested above, the organ culture process of the present invention is advantageous because:

1) organ culture is a form of self-immobilization which can allow the "reuse" of expensive biomass;

2) production of important flavorants for precooked and processed foods will be beneficial to the food industry;

3) secondary metabolites can be useful in pharmaceutical preparations.

EXAMPLES

The following examples are meant to generally illustrate the invention, not to limit it to any single root culture or organ. The invention is intended to apply to organ cultures generally. Accordingly, the invention should not be narrowly construed.

EXAMPLE 1

Root Culture Preparation

Root cultures for species with readily obtainable seeds, were prepared by first surface sterilizing seed material. Seeds were submerged in a 0.1% sterile benzylalkonium chloride solution. Following sonication for up to 5 minutes the liquid was decanted and 70% ethanol added to the seeds for up to 1 minute. Seeds were then treated with 0.5% sodium hypochlorite for 5 minutes, rinsed with deionized water several times and placed on BDS medium (no hormone) solidified with agar. After germinating for several weeks at 25° C. root tips of about 1 cm in length could be excised from the sterile plantelets.

Alternatively, when seeds were not available, shoot apical meristems were sterilely excised from mature bulbs or plants to obtain sterile and virus-free meristems. These were placed on agar solidified BDS with either no hormone or $10^{-6}$ M Indole Butyric Acid. On incubating at 25° C. for about 6 weeks the growing shoots developed roots which could then be excised for inoculation into liquid medium.

The sterile root tips, from either source, were placed in 50 ml Erlenmeyer flasks containing 10 ml of BDS medium with $10^{-6}$ M Indole Butyric Acid and cultured on a gyratory shaker, 100 rpm, at 25° C. for several weeks. Roots with associated lateral roots could then be transferred to BDS medium with sequentially higher IBA concentrations at 2 to 3 week intervals; typically from $10^{-6}$ to $10^{-5.5}$ to $10^{-5}$ to $10^{-4.5}$ M IBA (if necessary to optimize growth). Well developed root cultures were transferred at 2 week intervals at $10^{-5}$ or $10^{-4.5}$ M IBA.

EXAMPLE 2

Root Cultures

Using one or more of the procedures set forth in Example 1, root cultures were prepared as follows for 12 Allium species including *A. cepa; A. niponicum; A. sativum; A. wakegi; A. vineale: A. porrum; A. fistulosum; A. ascolonicum: A. bakeri; A. tuberosum; A. tricoccum;* and *A. schoenoprasum*. The various root cultures differ in growth rate, growth morphology, dry weight as a percent of fresh weight, total productivity, product profile, and % of product released to the medium. The properties of the various root cultures are given in Table 1.:

| PERFORMANCE OF Allium ROOT CULTURES | | | | |
|---|---|---|---|---|
| Root Culture | Total Prec. mg/g Fwt (b) | % in Medium | MCSO/ PECSO (a) | Growth td (days) |
| A. cepa #6 | .65 | 47.0 | .22 | 6.5 |
| A. cepa #7 | .55 | 97.1 | .87 | 10.1 |
| A. cepa NBR1 | .30 | 47.3 | — | 7.6 |
| A. cepa NBR2 | .22 | 52.3 | — | 7.0 |
| A. cepa sws' | .29 | 56.7 | 6.2 | 6.6 |
| A. cepa SWSN | .26 | 47.3 | .49 | 7.8 |
| A. fistulosum[1] | .38 | 22.8 | 1.6 | 10.1 |
| A. fistulosum[4] | .90 | 3.3 | 1.1 | 10.3 |
| A. fistulosum[5] | .47 | 27.2 | 2.2 | 9.5 |
| A. fistulosum[6] | .59 | 14.6 | .57 | 9.0 |
| A. niponicum | 1.02 | 8.2 | .70 | 7.5 |
| A. porrum | .51 | 63.5 | .17 | 7.8 |
| A. ursinum | .29 | 4.2 | .15 | 13.0 |
| A. wakegi #1 | .68 | 12.1 | .44 | 7.4 |
| A. wakegi #2 | .63 | 4.5 | .79 | 7.9 |

(a) Ratio of methyl cysteine sulfoxide to propenyl cysteine sulfoxide.
(b) Total flavor precursor - mg/g fresh weight.

In culturing root tips, it was found that the rate of growth for *A. cepa* #6 increased markedly when 2 percent glucose was substituted for 3 percent sucrose in the BDS growth medium.

EXAMPLE 3

Preparation of Flavor Precursors for Use As Standards

Prior to quantitation of flavor precursor concentrations in roots and in medium, samples standards had to be chemically synthesized as they were not available commercially. The cysteine sulfoxide derivatives of interest were made by: 1) derivatization of cysteine with either propyl, allyl, or butyl bromide (methyl and ethyl derivatives were purchased commercially), 2) isomerization of allyl to propenyl and, 3) hydrogen peroxide oxidation of all six cysteine derivatives. Identity of all compounds was confirmed by melting point, TLC, mass spectrometry and reactivity with allinase enzyme (using HPLC).

EXAMPLE 4

Feeding of Chemical Promoter Additive

The effects of several compounds on the production of flavor precursors by onion root cultures were tested by adding them directly to the BDS medium ($10^{-4.5}$ IBA) before autoclaving. Added were sodium sulfate, methionine and cysteine; and in equimolar ratios, cysteine plus valine, cysteine plus methacrylic acid, sulfate plus serine, sulfate plus valine, and sulfate plus methacrylic acid. Concentrations ranged from 1mM to, for sulfate, 100mM. Twenty five ml of medium was used for each 125 ml flask, and inoculum was about 1 g fresh weight of roots each. Flasks were incubated at 25° C. on a gyratory shaker, 100 rpm, for 10 days. Roots were then weighed, homogenized in TCA with 1 mg ethyl cysteine sulfoxide added as an internal standard.

Samples were then filtered, and applied to 4 ml columns of Dowex 50 w ion exchange resin (H+form). Columns were eluted with 11 ml of 2 M KOH and the last 9 ml collected. A saturated boric acid solution was added and the pH adjusted with conc HCl to pH 8.0. Two hundred $\mu$l of this solution was added to 200 $\mu$l of 4 mM FMOC in acetone and the amino acids allowed to react for 10 minutes. After extracting the mixture with 400 $\mu$l of pentane, the FMOC derivatives were subjected to isocratic reverse phase chromatography on a Waters 30 cm Nova Pak $C_{18}$ a column. The mobile phase consisted of acetonitrile and aqueous $PO_4$ (pH adjust), trisodium citrate (0.015M), and tetramethyl ammonium chloride (0.01M) buffer, pH 3.0 and pH 3.8. Retention times were compared with standards and flavor precursors quantitated according to their peak area relative to the ethyl cysteine sulfoxide internal standard.

Table 2 demonstrates that added methionine roughly doubled the level of the important propenyl cysteine sulfoxide and more than tripled the level of the methyl compound. Exogenously added cysteine also roughly doubled the propenyl compound but moreover resulted in a more than 10-fold increase in the important propyl compound and an eighteen fold increase in methyl compound. Precursor levels are not significantly enhanced unless a reduced sulfur source such as cysteine is added.

TABLE 2

| Additive* | | FEEDING OF BIOSYNTHETIC INTERMEDIATES | | | | | | | | | | | |
|---|---|---|---|---|---|---|---|---|---|---|---|---|---|
| | | Met | | | Cys | | | Cys + Val | | | Cys + MAA | | |
| mg/gm | Fwt | PE** | PR** | M** | PE | PR | M | PE | PR | M | PE | PR | M |
| 100 | mM | .504 | .053 | .094 | .504 | .053 | .094 | .504 | .053 | .094 | .504 | .053 | .094 |
| 1 | mM | .472 | .02 | .142 | .694 | .08 | .41 | .78 | .068 | .127 | .452 | .019 | .075 |
| 5 | mM | — | — | — | .604 | .231 | 1.60 | .643 | .196 | .438 | — | — | — |

TABLE 2-continued

| Additive* | | FEEDING OF BIOSYNTHETIC INTERMEDIATES | | | | | | | | | | |
|---|---|---|---|---|---|---|---|---|---|---|---|---|
| | | Met | | | Cys | | | Cys + Val | | | Cys + MAA | |
| mg/gm | Fwt | PE** | PR** | M** | PE | PR | M | PE | PR | M | PE | PR | M |
| 10 | mM | .96 | .022 | .34 | .865 | .554 | 1.70 | — | — | — | — | — | — |

*Chemical Additive: Methionine, Cysteine, Cysteine + Valine; Cysteine + Methacrylic Acid.
**Products:
PE = propenyl;
PR = propyl;
M = methyl Derivatives of cysteine sulfoxide (mg/gram fresh weight of root).

EXAMPLE 5

Transformation of a variety of Allium tissues with three Agrobacterium rhizogenes strains was attempted. Recent reports on the use of acetosyringone to aid in transformation (mobilization of the Ri plasmid for transfer) suggested that its use at 20 mM might enable transformation of this monocot genus (Stachel et al., 1985). It was hoped that successful infection would result in a "hairy root" phenotype with a high growth rate. However, despite the successful co-culture of bacteria with a variety of surface sterilized materials, no phenotypic response was observed over the course of two months.

Custom Synthesis of Flavor Precursors and Flavors

The sulfur containing secondary metabolites of onion, garlic and related Allium species are of considerable interest for food and pharmaceutical use. Especially for food processing applications, a secure and continuous supply of consistently high quality flavors is required. In one aspect, the present invention relates to use of Allium plant cell cultures and more specifically differentiated root organ cultures to produce secondary metabolites such as the flavor precursors (+)S-alk(en)yl-L-cysteine sulfoxides (RCSO's) which, though possessing little odor or flavor themselves, are converted to active flavor compounds upon contact with allinase enzyme. Allinase, believed to be compartmentalized into a vacuole, normally only comes into contact with RCSO's when it is released by cell damage. The principle RCSO's S-alk(en)yl cysteine sulfoxides are S-methyl cysteine sulfoxide (MCSO); S-ethyl cysteine sulfoxide (ECSO); S-allylcysteine sulfoxide (ACSO); trans S-(1-propenyl) cysteine sulfoxide (PECSO); S-propyl cysteine sulfoxide (PRCSO) and O-acetyl serine (OAS). One objective was to determine the effect on total and relative RCSO levels, of adding sulfate, valine, methacrylic acid, serine, cysteine, methionine, glutathione and the thiols including, propyl, allyl and ethyl thiol. The objective was to not only enhance the quantity of RCS production, but also to control the quality of flavor products by controlling the ratios of flavor precursor moities (flavor profile manipulation) produced by the root organ culture through selective addition of chemical additives. Thus the invention allows the enhancement or suppression of specific flavor precursors, permitting customized flavor production (by further reaction with enzyme). By proper selection of chemical additives to root culture medium, flavor precursors and flavors can be produced by root biosynthesis, which are uncharacteristic of and different from those occurring naturally in the respective Allium plant (bulb, shoot, etc).

Cysteine, Glutathione and Methionine

Figure 4:
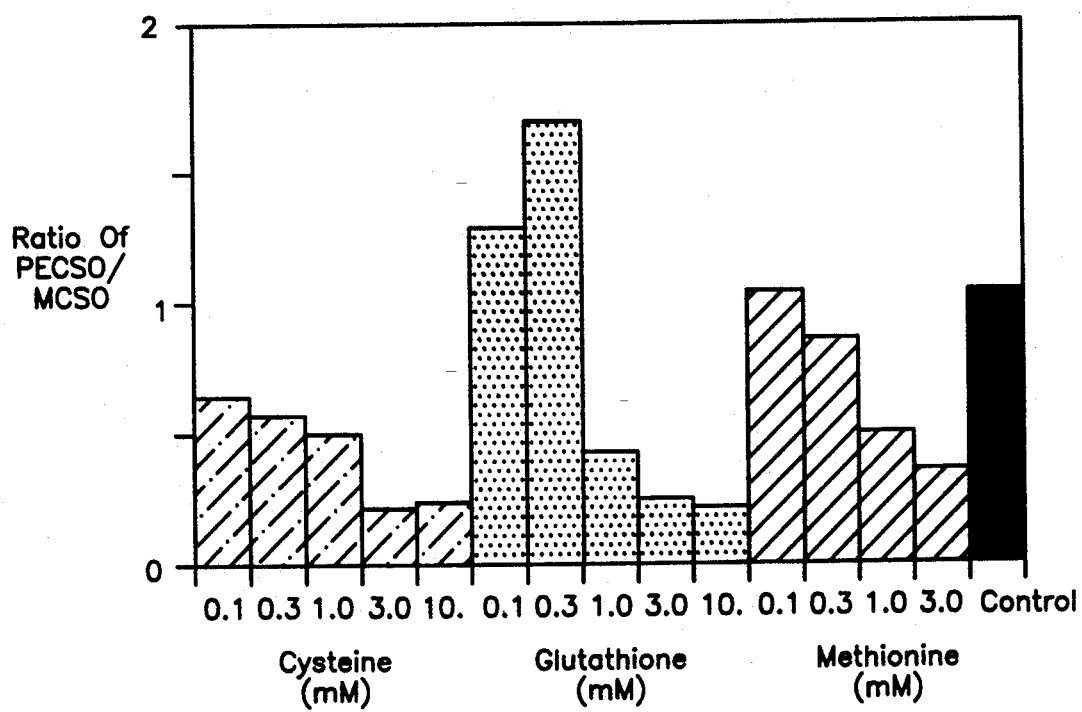
FIG. 4 is a plot showing the effects on alk(en)yl cysteine sulfoxide (RCSO) product distribution (Ratio of PECSO/MCSO where PE=propenyl and M=methyl substitution of the sulfur), for 0.1, 0.3, 1.0, 3.0 and 10 mM additions of cysteine, glutathione and methionine additives to onion root culture medium.

The effects of cysteine, glutathione and methionine addition are shown in FIG. 4. As is often the case in intact A. cepa plants, PRCSO (S-propyl) levels were observed to be low and are therefore not shown. However, significant increases in both MCSO (S-Methyl) and PECSO (S-propenyl) concentrations are observed, depending on the treatment.

With cysteine addition, FIG. 4 shows that incorporation into either MCSO or PECSO is possible. Exogenous cysteine empirically has the effect of increasing MCSO accumulation by a factor of 2 to 3 (over 10-fold on a per gram fresh weight basis) and yet a somewhat inhibitory effect on PECSO biosynthesis; it is a plausible inference that, under the current conditions, cysteine is preferentially incorporated into MCSO.

As a tripeptide containing cysteine, one might anticipate that glutathione would mimic cysteine in its influence over RCSO levels. FIG. 4 suggests, however, that glutathione lies directly on the path to PECSO biosynthesis and that incorporation into MCSO should depend entirely on the relative rate of glutathione decomposition to cysteine. Interestingly, an approximately 2-fold increase in PECSO is observed at the 0.3 mM level; glutathione evidently behaves quite differently from cysteine at low concentrations With 3 and 10 mM glutathione spikes, however, the response was almost identical to that of cysteine, suggesting that glutathione back-conversion to cysteine dominates at higher concentrations The predominant effect of methionine was, as expected, to increase MCSO levels as is most clearly seen at the 3 mM level. Some enhancement in PECSO biosynthesis is also observed at lower concentrations.

The value of feeding cysteine, metionine and glutathione for flavor profile manipulation is shown in FIG. 4, which indicates that at least an 8.5-fold difference in the ratio of PCSO:MCSO is possible. Importantly for both productivity enhancement and profile manipulation, the experiments spanned a period in batch growth corresponding to only the lag phase (up to 5 days) and 2 to 3 days of the rapid growth phase. Subsequent time course studies indicate that neither MCSO nor PECSO are normally synthesized in the lag phase and only MCSO appears during rapid growth in short term batch runs. Considering this, treatment during a much later phase in batch might well have given rise to more pronounced productivity enhancements and PECSO-MCSO deviations.

Thiols as Chemical Additives

A further aspect of the invention relates to a process for enhancing in a culture medium the exogenous production of alk(en)yl cysteine sulfoxides (RCSO) or mixtures thereof having the structure:

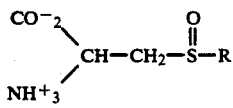

where R represents a $C_{1-20}$ alkyl, alkylene, or cycloalkyl radical and mixtures thereof which comprises:
1) culturing a root derived differentiated Allium root culture in a culture medium conducive to predominantly root growth; and
2) adding to said culture medium one or more chemical additives selected from the group consisting of alkyl, alkylene or cycloalkyl thiols in an amount sufficient to enhance the production of the corresponding RCSO or mixture thereof in said medium.

When Allium type flavors and flavor precursors are desired, then it is preferred to add to the root culture medium, as chemical additives, $C_{1-6}$ thiols and preferably thiols selected from the group consisting of methylthiol, ethylthiol, propylthiol, propenylthiol and allylthiol and/or mixtures thereof in an amount sufficient to enhance the production of the corresponding RCSO or mixtures thereof having desired flavor characteristics.

The addition of thiol additives to the root culture medium gave enhanced exogenous production of alk(en)yl cysteine sulfoxides (RCSO) or mixtures thereof having the structure (II) where R represents a methyl, ethyl, propyl, propenyl or allyl radical. By selection of the thiol additive one can custom direct to specific cysteine sulfoxides or mixtures thereof and thus predetermine the flavor characteristics of the RCSO (Allium flavor precursors) produced. The selectivity can be controlled by the choice of the root type and by the type and amount of chemical additive (thiol) added to the root culture medium to produce novel flavor precursors, flavors and hybrid mixtures which are not known or produced per se in nature. For example, using an onion root culture and allylthiol as additive, it is possible to produce flavor precursor RCSO's having allyl substitution (S-allyl). Thus flavor characteristics representative of garlic can be obtained from onion root which are not known to produce garlic type flavor precursors and flavors. This method is advantageous in predetermining the flavor spectrum of the products and allows one to custom produce flavor precursor and flavors by appropriate selection of Allium root and chemical additive. Similar custom product predetermination can be effected using methyl, ethyl, propyl, propenyl, and allyl thiols to produce S-methyl, S-ethyl, S-propyl, S-propenyl, and S-allyl derivatives of cysteine sulfoxide. Further, the Allium root can be selected from any of the newly produced differentiated root organ culture selected from the group consisting of *A. niponicum; A. wakegi; A. vineale; A. porrum; A. fistulosum; A. ascolonicum; A. tuberosum; A. tricoccum*; and *A. schoenoprasum*. By proper selection of one or more chemical additives to the root organ culture medium, the ratio of S-substituted (methyl, ethyl, propyl, allyl, etc.) product RCSO's can be modified within wide limits to produce flavor precursors (and flavors) and mixtures not previously known in the plant system.

Substituting other $C_{1-20}$ thiol additives will produce RCSO's having the corresponding S-substituents with corresponding characteristic flavor properties.

Directed biosynthesis is an exciting route to productivity enhancement, and to profile manipulation for quality maximization and the "tailoring" of natural flavors for specific process applications.

EXAMPLE 6

Root cultures were initiated and subcultured as described above. Experiments were conducted using an *Allium cepa* root line initiated from seeds of a green onion variety (Takii Seed Corporation, Kyoto Japan). Routine subcultures were of 1.5 grams fresh weight into 5.0 ml liquid BDS salt medium (Dunstan and Short, 1977) with 2% glucose and 30 $\mu$M indole butyric acid in a 250 ml flask. Cultures were incubated in the dark for 2 weeks at 25° C. on a gyratory shaker (100 rpm).

Feeding experiments using propanethiol, ethanethiol and allylthiol were carried out using 1.01±0.04 g fresh weight root culture in 25 ml nutrient medium in 125 ml conical flasks. Conditions were otherwise as above, except for the addition of precursors and the use of filter sterilization instead of autoclaving. Cultures were recovered after 1 week, weighed and extracted as indicated above.

RCSO Analysis

RCSO's were quantitated using a reverse phase HPLC method employing precolumn FMOC-Cl derivatization. Synthetic (±) S-ethyl cysteine sulfoxide was used as an internal standard except in the case of ethanethiol addition where, instead S-carboxymethyl cysteine was substituted.

Figure 5A:
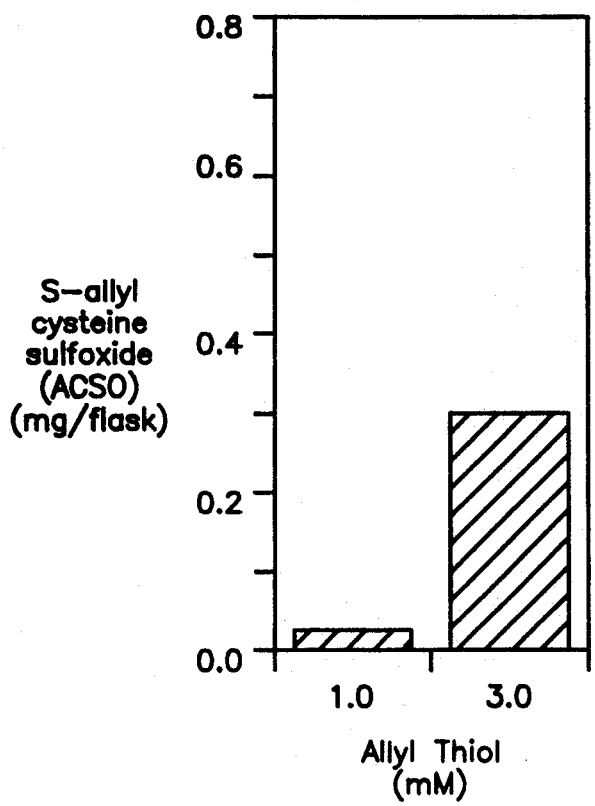
FIG. 5A is a plot showing the effects on exogenous allylcysteine sulfoxide (ACSO) production with 1.0 and 3.0 mM additions of allylthiol to the root culture medium.
Figure 5B:
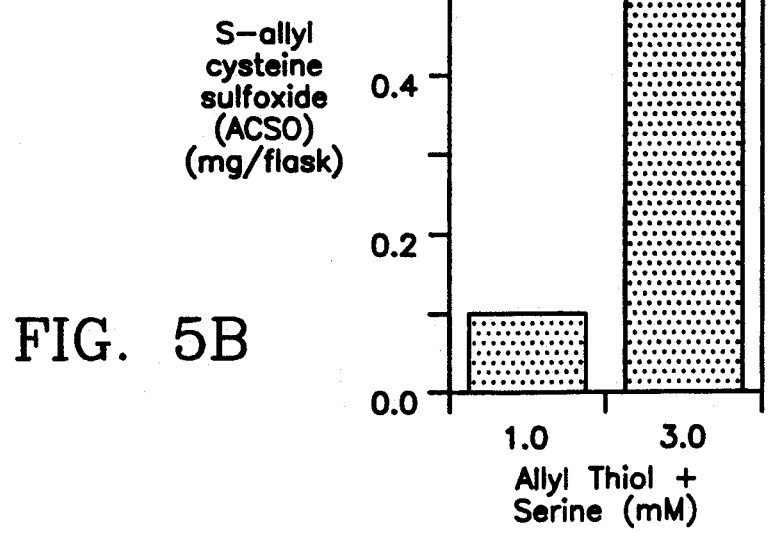
FIG. 5B is a plot showing the effects on exogenous allylcysteine sulfoxide (ACSO) production with the combined additions of 1.0 and 3.0 mM of allylthiol and serine.
Figure 6:
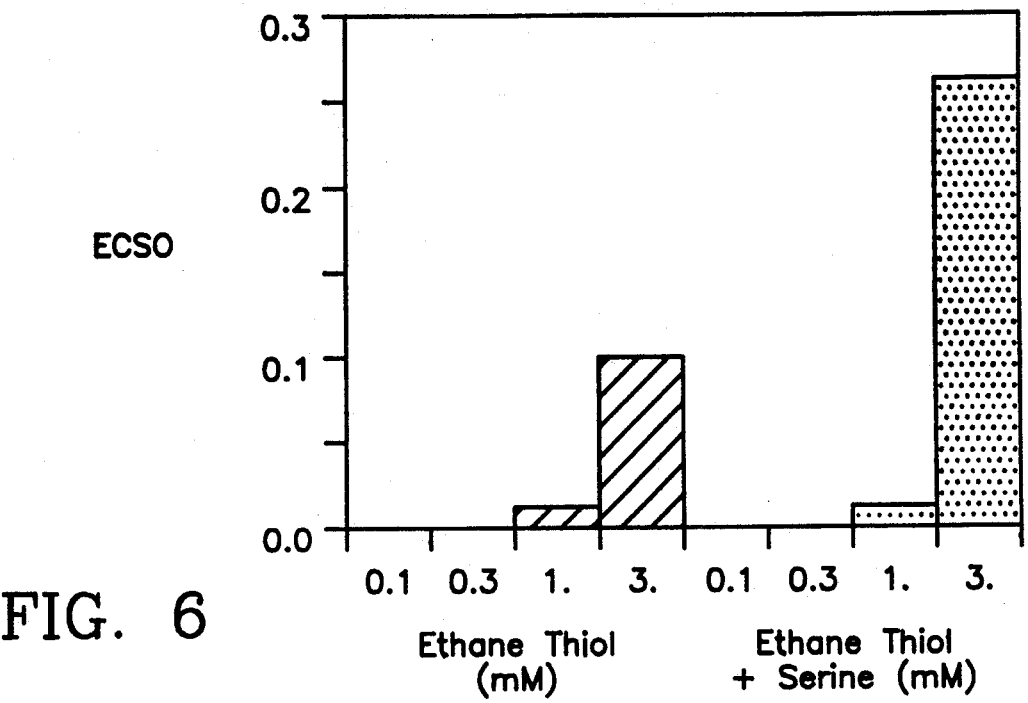
FIG. 6 is a plot showing the effect of addition of ethylthiol and ethylthiol plus serine on exogenous production of S-ethylcysteine sulfoxide (ECSO) from *A. cepa* differential root.
Figure 7:
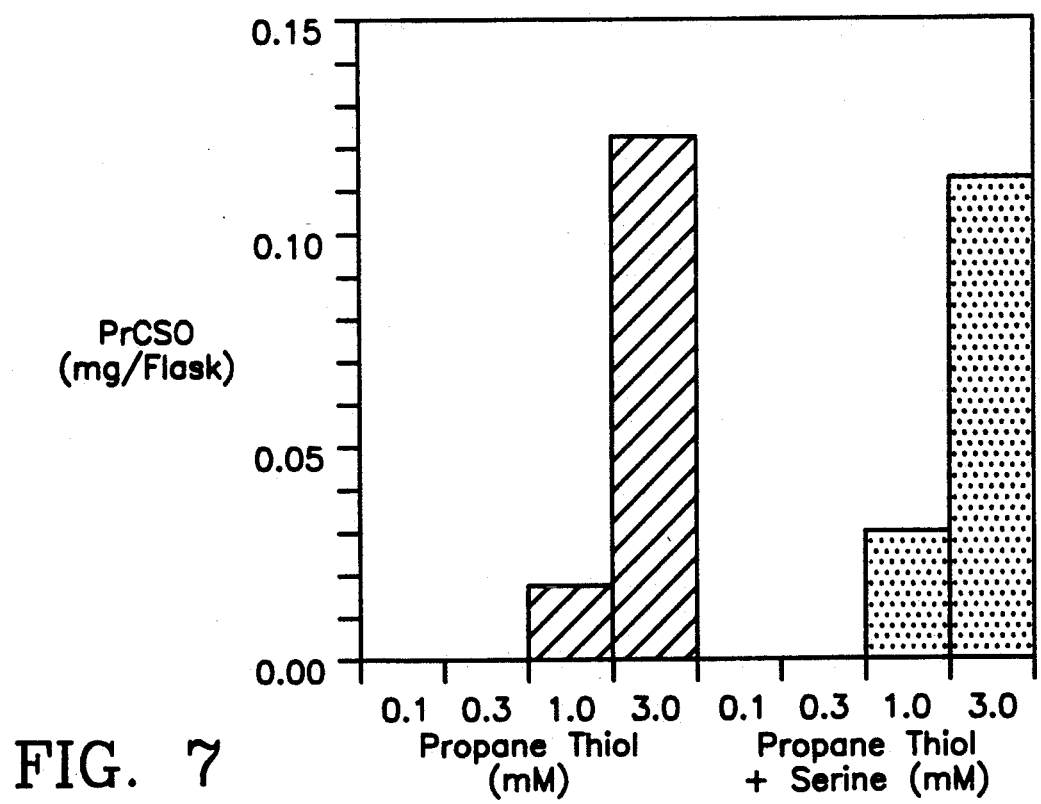
FIG. 7 is a plot showing the effect of addition of propylthiol and propylthiol plus serine on the exogenous production of s-propylcysteine sulfoxide (PRCSO) from *A. cepa* differentiated root.

As shown in FIGS. 5, 6 and 7 allylthiol, ethylthiol and propylthiol were effectively incorporated into the corresponding alk(en)yl cysteine sulfoxide. Only the naturally occurring (+) diastereomers were biosynthesized.

These results are exciting in that PRCSO (S-propyl) is normally produced only in low amounts, ACSO (S-allyl) is normally produced by garlic and not onion, and ECSO (S-ethyl) is not known to be produced by any Allium sp. at all. Through directed biosynthesis it is not only possible to manipulate levels of normal flavor constituents, but also to create novel flavor "hybrids" such as garlic/onion, and even to create flavor compounds with entirely novel side chains. Such control over secondary metabolite profiles is not possible with agricultural approaches.

EXAMPLE 7

Allylthiol Additive

Using the root biosynthesis process described above, allylthiol was added to differentiated root cultures of *A. cepa*. A plot of the production (exogenous) of S-allyl cysteine sulfoxide (ACSO) with 1.0 and 3.0 millimole allylthiol additive, in an onion root culture is shown in FIG. 5A. The addition of 1.0 millimole produces about 0.02 mg ACSO per flask in a five-day reaction time and gives 0.3 mg ACSO when allylthiol is added at 3.0 millimole.

EXAMPLE 8

Mixture of Allylthiol and Serine

Using the root biosynthesis process described above, a mixture of allylthiol and serine was added to the differentiated root cultures of *A. cepa*. A plot of the production (exogenous) of S-allyl cysteine sulfoxide (ACSO) is shown in FIG. 5B where the combined addition of 1.0 millimole of allylthiol plus 1.0 millimole of serine with onion root culture produces even higher amounts of S-allyl cysteine sulfoxide (ACSO) (ca 0.1 mg/flask) while the addition of 3.0 millimole of both allylthiol plus serine increases the yield of ACSO to about 0.7 mg/flask.

EXAMPLE 9

Using the biosynthesis process described above, ethylthiol and a mixture of ethylthiol and serine were added to the differentiated organ root cultures of *A. cepa*. A plot of the production (exogenous) of S-ethylcysteine sulfoxide (ECSO) is shown in FIG. 6. As seen in FIG. 6, the amount of ECSO increases about 80 percent with 1 and 3 millimole addition of ethylthiol and about 80% when equimolar amounts of ethylthiol and serine (1,3 mM) are added to root culture medium.

EXAMPLE 10

Using the biosynthesis process described above, propylthiol and a equimolar mixture of propylthiol and serine were added at 1 and 3 millimole levels to the differentiated organ root cultures of *A. cepa*. A plot of the production (exogenous) of S-propylcysteine sulfoxide (PRCSO) is shown in FIG. 7. The addition of propylthiol produces about 0.02 mg PRCSO per flask for 1 mM addition and about 0.14 mg at 3 mM addition.

The equimolar mixture of propylthiol and serine gives about 0.03 mg PRCSO product at 1 mM additive and about 0.11 mg PRCSO at 3 mM addition.

What is claimed is:

1. A process for the exogenous production of at least one flavor precursor selected from the group consisting of S-methyl, S-ethyl, S-propyl, S-propenyl and S-allyl cysteine sulfoxides, said process comprising the steps of:
    a) culturing a sterile and virus-free Allium shoot apical meristem to produce a plantlet;
    b) excising a root tip from said plantlet; and
    c) culturing the root tip in the presence of an auxin selected from the group consisting of indole butyric acid, 4-chloroindole acetic acid and 5,6-dichloroindole acetic acid at a concentration of 0.01 to 10 mg/l of culture medium such as to promote the formation and growth of a viable and genetically stable differentiated cultured root with lateral branches to the exclusion of callus growth and to produce and excrete said flavor precursor.

2. A process for the exogenous production of at least one flavor precursor selected from the group consisting of S-methyl, S-ethyl, S-propyl, S-propenyl and S-allyl cysteine sulfoxides, said process comprising the steps of:
    a) germinating a sterilized Allium seed and culturing the seed in a hormone-free nutrient medium to produce an Allium plant comprising a root;
    b) excising a root tip from the root;
    c) culturing the excised root tip in the presence of an auxin selected from the group consisting of indole butyric acid, 4-chloroindole acetic acid and 5,6-dichloroindole acetic acid at a concentration of 0.01 to 10 mg/l of culture medium such as to promote the formation and growth of a viable and genetically stable differentiated cultured root with lateral branches to the exclusion of callus growth and to produce and excrete said flavor precursor.

3. The process of claim 1 wherein the auxin is indole butyric acid.

4. The process of claim 2 wherein the auxin is indole butyric acid.

* * * * *

UNITED STATES PATENT AND TRADEMARK OFFICE
CERTIFICATE OF CORRECTION

PATENT NO. : 5,244,794

DATED : September 14, 1993

INVENTOR(S) : Christopher Prince et al

It is certified that error appears in the above-identified patent and that said Letters Patent is hereby corrected as shown below:

On the title page: Item [56]

under "OTHER PUBLICATIONS" list additionally:

-- Shuler, M. L., et al, "Bioreactor Considerations for Producing Flavors and Pigments from Plant Tissue Culture", Chapter 3, pp. 45-66, in Biotechnology and Food Process Engineering, editors Schwartzby and Rao, M. A. Marcel Dekker, Inc., 1990 --.

Signed and Sealed this

Sixteenth Day of August, 1994

*Attest:*

BRUCE LEHMAN

*Attesting Officer*     *Commissioner of Patents and Trademarks*